(12) United States Patent
Kvaale et al.

(10) Patent No.: US 7,922,707 B2
(45) Date of Patent: Apr. 12, 2011

(54) DEVICES AND METHOD FOR THE PENETRATION OF A CONTAINER STOPPER

(75) Inventors: Svein Kvaale, Oslo (NO); Thor Audun Saga, Oslo (NO)

(73) Assignee: GE Healthcare AS, Oslo (NO)

( * ) Notice: Subject to any disclaimer, the term of this patent is extended or adjusted under 35 U.S.C. 154(b) by 494 days.

(21) Appl. No.: 11/156,311

(22) Filed: Jun. 17, 2005

(65) Prior Publication Data
US 2006/0229584 A1    Oct. 12, 2006

(30) Foreign Application Priority Data
Mar. 24, 2005    (GB) .................. 0506057.9

(51) Int. Cl.
*A61M 5/32* (2006.01)
*A61M 5/30* (2006.01)
*B65D 55/00* (2006.01)
*B65D 51/00* (2006.01)
*B65D 51/18* (2006.01)
*B65D 41/32* (2006.01)

(52) U.S. Cl. ........ 604/411; 604/413; 604/414; 604/415; 604/905; 604/68; 220/229; 220/260; 220/256; 220/266; 220/200

(58) Field of Classification Search ............... 604/411, 604/413, 414, 415, 403, 903, 905, 68; 220/229, 220/260, 265, 266, 200
See application file for complete search history.

(56) References Cited

U.S. PATENT DOCUMENTS

| | | | |
|---|---|---|---|
| 4,236,520 A | 12/1980 | Anderson | |
| 4,534,465 A * | 8/1985 | Rothermel et al. | 206/443 |
| 4,582,223 A * | 4/1986 | Kobe | 222/82 |
| 4,834,152 A * | 5/1989 | Howson et al. | 141/286 |
| 4,838,877 A | 6/1989 | Massau | |
| 4,959,053 A * | 9/1990 | Jang | 604/127 |
| 5,037,390 A * | 8/1991 | Raines et al. | 604/83 |
| 5,279,576 A * | 1/1994 | Loo et al. | 604/187 |
| 5,324,483 A * | 6/1994 | Cody et al. | 506/40 |
| 5,423,753 A * | 6/1995 | Fowles et al. | 604/87 |
| 5,478,328 A | 12/1995 | Silverman | |
| 5,509,912 A * | 4/1996 | Vaillancourt et al. | 604/537 |
| 5,531,672 A * | 7/1996 | Lynn | 604/6.12 |
| 5,609,826 A * | 3/1997 | Cargill et al. | 422/99 |
| 5,848,996 A | 12/1998 | Eldor | |
| 5,976,470 A * | 11/1999 | Maiefski et al. | 422/103 |
| 6,032,812 A | 3/2000 | Lamoureux | |
| 6,126,904 A * | 10/2000 | Zuellig et al. | 422/130 |
| 6,221,056 B1 | 4/2001 | Silverman | |
| 6,319,399 B1 * | 11/2001 | Peterson et al. | 210/232 |
| 6,398,956 B1 * | 6/2002 | Coville et al. | 210/321.75 |
| 6,416,718 B1 * | 7/2002 | Maiefski et al. | 422/103 |
| 6,485,690 B1 * | 11/2002 | Pfost et al. | 422/102 |
| 6,527,758 B2 * | 3/2003 | Ko | 604/403 |
| 6,783,732 B2 * | 8/2004 | Madden et al. | 422/63 |
| 7,341,872 B1 * | 3/2008 | Anderson et al. | 436/43 |
| 2004/0254541 A1 * | 12/2004 | Wong et al. | 604/239 |
| 2008/0156377 A1 * | 7/2008 | Mann | 137/263 |

* cited by examiner

Primary Examiner — Leslie R Deak
Assistant Examiner — Adam Marcetich
(74) Attorney, Agent, or Firm — Robert F. Chisholm

(57) ABSTRACT

A spike for penetrating the elastomeric stopper of a container, for example a drug or reagent vial, is provided with an elongated body (5) with a blunt tip (47). The spike may be incorporated into a reagent cassette which accepts containers sealed with a punturable cap.

14 Claims, 4 Drawing Sheets

DEVICES AND METHOD FOR THE PENETRATION OF A CONTAINER STOPPER

FIELD OF THE INVENTION

The present invention relates generally to devices and methods for penetrating stoppers. More specifically, the present invention is directed to an improved spike for a reagent cassette.

FIELD OF THE INVENTION

Medical drugs, reagents and other substances are often supplied in metal, glass or plastic containers. These containers have a hollow body connected to a neck which has a radially extending flange. The neck has a central passage which extends in the longitudinal direction of the container from the flange to the inside of the body. The central passage in the neck may be sealed by a rubber, plastic or other elastomeric stopper or septum. As is known in the art, the stopper may be retained by a retaining band folded over the flange, or a screw top, or shrink wrapping, or welding or the like. The stopper usually has a thin central portion which facilitates insertion of a cannula or hollow spike though the stopper. For the sake of brevity, the word "spike" will be used in this application to denote any device intended to pierce the stopper of a container and provide a passage which the contents of the container may travel through. The thin portion of the stopper is surrounded by a thick portion which is in contact with, and seals against, the inside wall of the central passage. If a retaining cap is used then it may be provided with a central opening aligned with the passage. When the contents of the container are to be extracted a spike is pressed in the longitudinal direction of the container through the opening in the retaining cap, if present, and into and through the elastomeric stopper until the tip of the spike is inside the container. The contents of the container may then be extracted through the spike. FIG. 1 a) shows an example of a spike correctly inserted into a stopper.

In an automated synthesizer unit with syringe plunger actuators and valve actuators for the automatic transfer of reagents from containers in the fluid path of the reagent cassette used in the synthesizer unit, it has been found that if a reagent cassette spike is made of a semi rigid polymer for example a polyolefin such as polypropylene, polyethylene or polycarbonate, and in particular if the passage in the neck of the container is narrow which necessitates a correspondingly thin spike, then during automated spiking, the spike may fail to penetrate cleanly though the thin portion of the stopper and instead bends to one side. It may come to rest in the thicker portion of the stopper, thereby blocking the spike and preventing extraction of the contents of the container. FIG. 1b) shows an example of a spike incorrectly inserted in a stopper.

SUMMARY OF THE INVENTION

The present invention provides a spike for penetrating a container stopper, wherein the spike has an elongated body defining a longitudinal bore. The body also includes a blunt tip.

The present invention also provides a reagent cassette which includes at least one spike of the present invention for penetrating a stopper.

The present invention further provides a method for penetrating the stopper of a container insertable into a reagent cassette. The method includes the steps of a) providing a reagent cassette with a spike of the present invention, b) aligning the longitudinal axis of the stopper with the longitudinal axis of the spike, and c) moving the spike and stopper towards each other until the spike has penetrated the stopper.

The present invention still further provides an improved spike. The spike includes a free end, a fixed end, and an elongate hollow body extending between. The body defines a longitudinal passageway there through as well as an aperture in fluid communication with and extending transversely to the passageway. The improvement includes forming the free end of the body to have a substantially flat surface extending transversely to the longitudinal axis of the body.

Even still further, the present invention provides an improvement to a cassette adaptable to be received by a automated synthesis unit. The cassette includes an elongate body accommodating components of fluid circuitry. The body also defines at least one receptacle for receiving a container having a puncturable cap. The receptacle includes a spike for puncturing the puncturable cap of the container so as to render the interior of the container in fluid communication with at least a part of the fluid circuitry. The improvement includes providing a spike including a blunt tip which is symmetrical about the longitudinal axis of the spike for penetrating puncturable stopper.

DETAILED DESCRIPTION OF PREFERRED EMBODIMENTS OF THE INVENTION

Figure 1A:
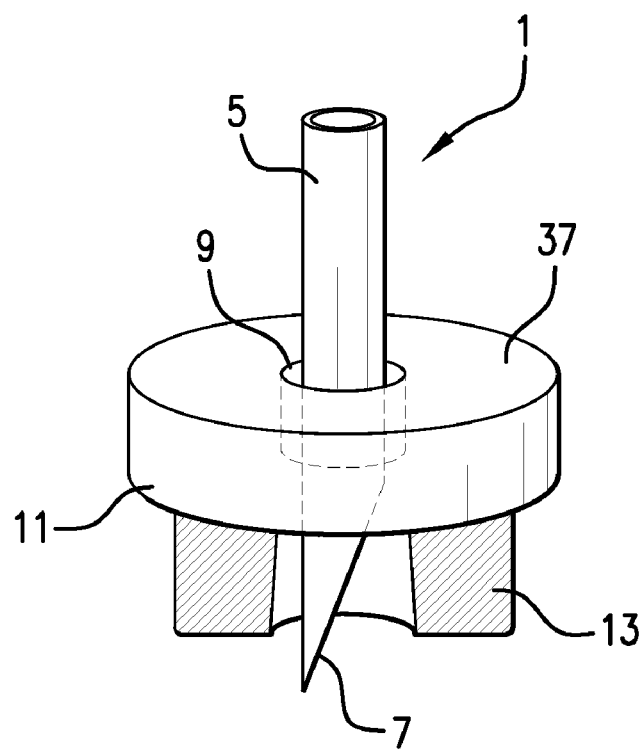
FIG. 1a) shows schematically a successful insertion of a spike of the prior art through a stopper.

FIG. 1a) shows schematically a perspective view of a successful insertion of a polyolefin spike 1 through a stopper 37. Spike 1 has an elongated tubular body 5 with a bevelled tip 7. Stopper 37 has a circular shape and has a thin central portion 9 of diameter S, a thin peripheral portion 11 and a thicker intermediate portion 13 between the central and peripheral portions 9, 11. In this figure, the bevelled tip 7 has passed in a vertical straight line through the thin central portion 9 of the stopper 37 and the tip 7 is exposed.

Figure 1B:
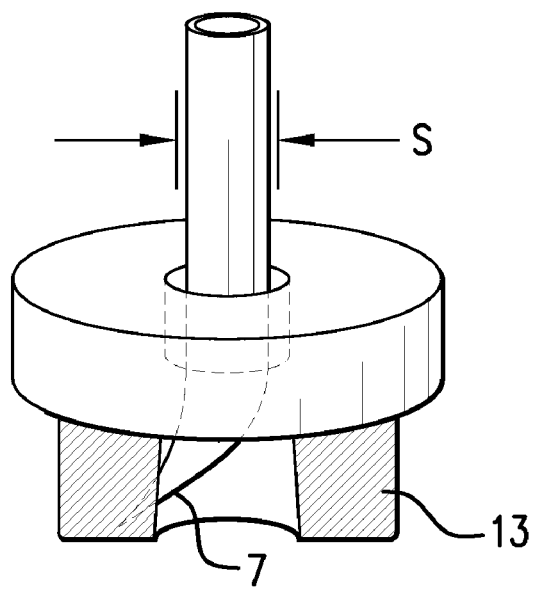
FIG. 1b) shows schematically an unsuccessful insertion of a spike of the prior art through a stopper.

FIG. 1b) shows schematically a perspective view of an unsuccessful insertion of a spike 1 through a stopper 37. In this figure, the bevelled tip 7 has been deflected off a vertical path through the central portion 9. Instead, it has followed a curved path which has resulted in the tip 7 becoming embedded in the thicker intermediate portion 13 of the stopper.

Figure 2A:
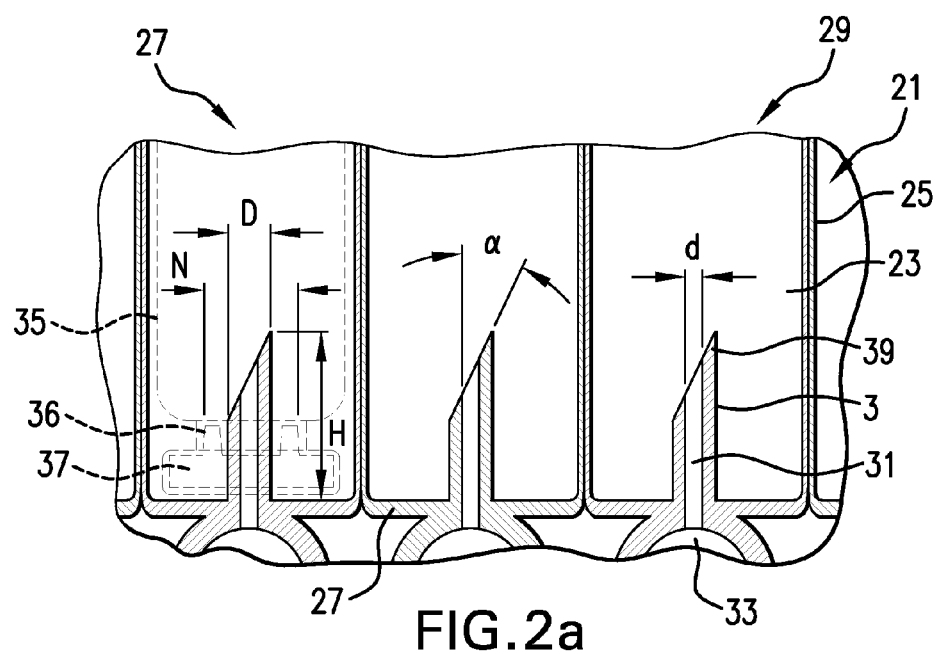
FIG. 2a) shows schematically a cross-section though a portion of a reagent cassette comprising a plurality of a spike of the prior art.
Figure 2B:
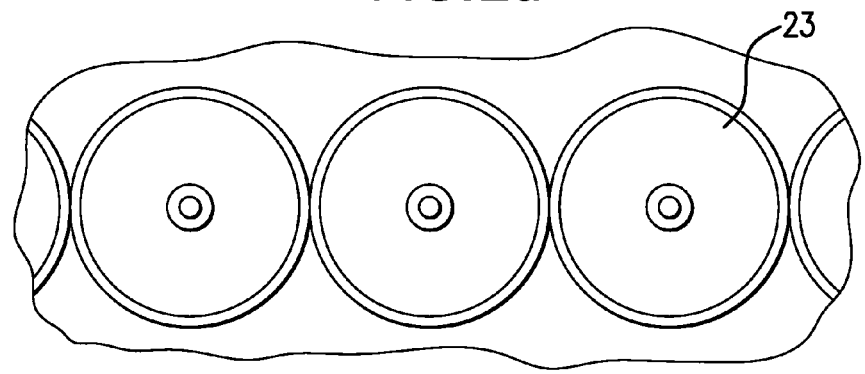
FIG. 2b) shows schematically a plan view of the portion of the reagent cassette of FIG. 2a)

FIG. 2a) shows schematically a cross-section though a portion of a reagent cassette 21 comprising a plurality of polyolefin spikes 3. Cassette 21 comprises a plurality of reagent container receiving chambers 23, each of which is surrounded by a wall 25. The base 27 of each chamber supports a centrally positioned spike 3 of outer diameter D and height H that projects along the central axis of the chamber towards the opposite, open end 29 of the chamber 23. Each spike 3 has a central bore 31 of diameter d which extends the whole length of the spike, though the base 27 of the reagent container receiving chamber and opens out into a valve 33. Valve 33 can be used to control the movement of fluids in central bore 31. A reagent container 35 is shown in dotted lines positioned in a reagent container receiving chamber 23. The size and shape of reagent container 35 and the size and shape of reagent container receiving chamber 23 are adapted so that reagent container 35 fits concentrically into reagent container receiving chamber 23 and is retained by friction between the reagent container and container wall 25. Container 35 has neck 36 with an inner diameter N which is greater than the outer diameter D of spike 3. Neck 36 is sealed by a stopper 37. The distance from outer surface of the stopper to the interior of the container is less than the height H of a spike 3. The tip 7 of each spike which is intended to pierce a stopper 37 is bevelled at an angle α° to form a sharp tip 7 with an inclined surface 39 which is inclined at the angle α° to the longitudinal axis of the spike.

Figure 3:
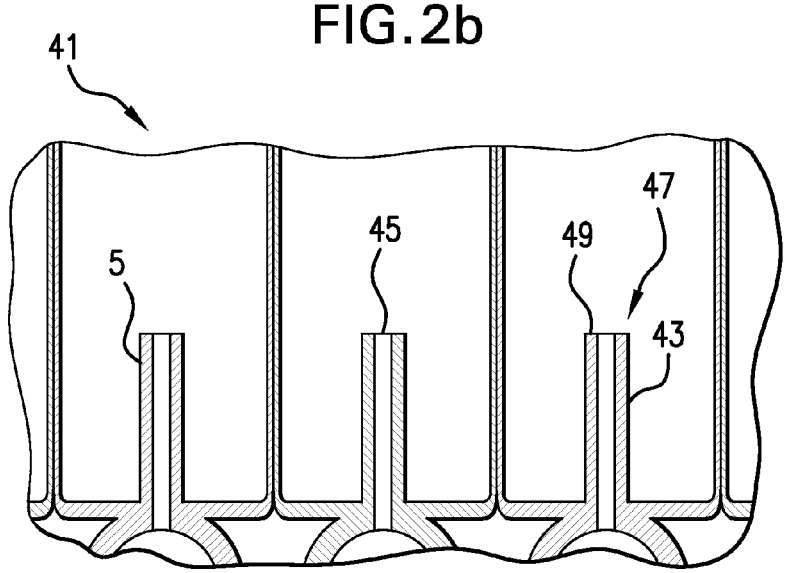
FIG. 3 shows a portion of an embodiment of a reagent cassette comprising a spike in accordance with one embodiment of the present invention.

FIG. 3 shows schematically a cross-section through a portion of a reagent cassette 41 comprising a plurality of semi-rigid spikes 43, made from, for example, polyolefins, in accordance with a first embodiment of the present invention. In this embodiment of the present invention, spikes 43 have open blunt tips 47 which are intended to penetrate the stopper 37 of a container—the end surface 49 of each tip 47 is substantially flat and arranged to be substantially perpendicular to the longitudinal axis of the elongated body 5 and has a central opening 45 communicating with central bore 31.

Figure 4:
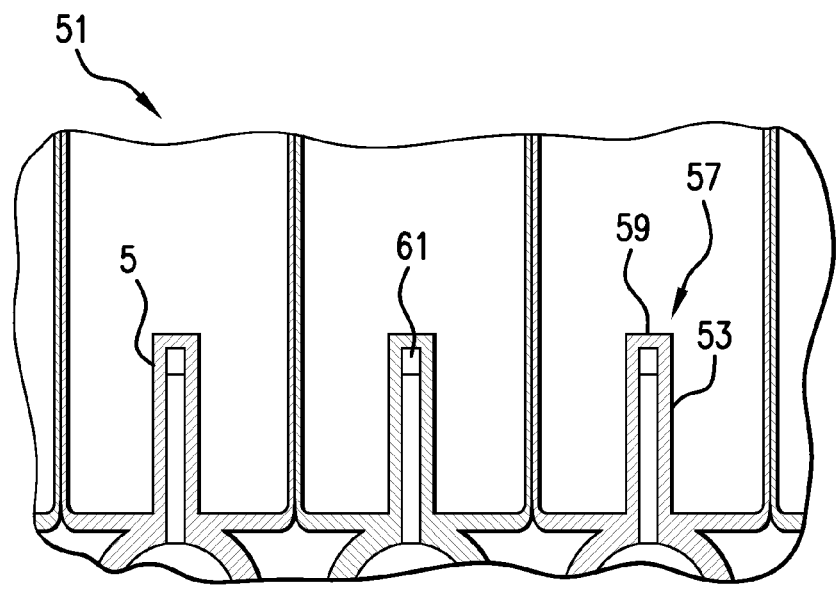
FIG. 4 shows a portion of an embodiment of a reagent cassette comprising a spike in accordance with a further embodiment of the present invention.

FIG. 4 shows schematically a cross-section through a portion of a reagent cassette 51 comprising a plurality of spikes 53 in accordance with a second embodiment of the present invention. In this embodiment of the present invention, spikes 53 have solid blunt tips 57 which are intended to penetrate the stopper of a container—the end surface 59 of each tip 57 is substantially flat, has no opening and is arranged to be substantially perpendicular to the longitudinal axis of the body 5. In order to allow fluid to enter a spike 53, each spike is provided with at least one lateral opening, for example a rectangular slit 61, which extends in the longitudinal direction of the spike from behind the solid tip 57 towards the opposite end of the spike and is in fluid communication with the central bore 31 blocked by solid end surface 59. Preferably the size and shape of each opening is adapted so that when the spike is inserted though a container stopper to its maximum depth, the whole of the opening is exposed to the interior of the container. Preferably each spike has two, three, four or more than four openings. Openings can be any shape, for example rectangular, square, round, oval.

The stopper of a reagent container can be penetrated in a reagent cassette in accordance with the present invention by placing the container in a container receiving chamber of the cassette with the stopper facing towards the spike, the longitudinal axis of the stopper being substantially aligned with the longitudinal axis of the spike, and then pressing the container towards the base of the chamber. As the container moves towards the base of the chamber, the blunt tip of the spike penetrates the stopper. The movement of the container is continued until the opening in the spike has penetrated all the way through the stopper and is exposed to the contents of the container.

Figure 5A:
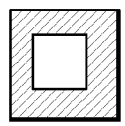
FIGS. 5a)-5d) show examples of possible spike transverse cross-sections.
Figure 5B:
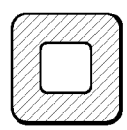
Figure 5C:
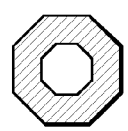
Figure 5D:
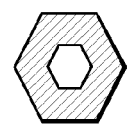

The transverse cross-sections of the spikes do not have to be circular. FIGS. 5a)-5d) shows a selection of further possible embodiments of spike cross-sections—quadratic, quadratic with rounded corners, octagonal and hexagonal respectively. Other cross-sections are also possible, preferably they are symmetrical about the longitudinal axis of the spike so that during penetration of a stopper by the spike the occurrence of undesirable lateral forces (that is forces perpendicular to the direction of relative movement between the stopper and spike) is avoided.

Figure 6A:
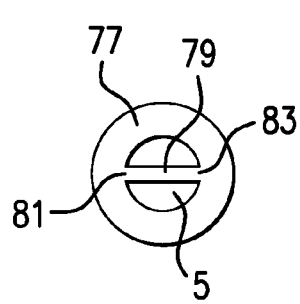
FIGS. 6a) and 6b) show plan views of examples of possible spikes.
Figure 6B:
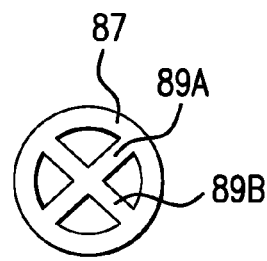

FIG. 6a) shows an enlarged schematic plan view of a further embodiment of a spike in which the spike tip 77 has a reinforcing transverse rib 79 that extends from one side 81 of the bore 5 to the diametrically opposite side 83. FIG. 6) shows an enlarged schematic plan view of a further embodiment of a spike in which the spike tip 87 has two, mutually perpendicular reinforcing transverse ribs 89A, 89B, each of which extends from one side of the bore 5 to the diametrically opposite side. While the above two embodiments of bores provided with reinforcing ribs have been illustrated with bores and tips with circular cross-sections, it is conceivable to use such ribs with bores and tips of any cross-sectional shape.

Figure 7:
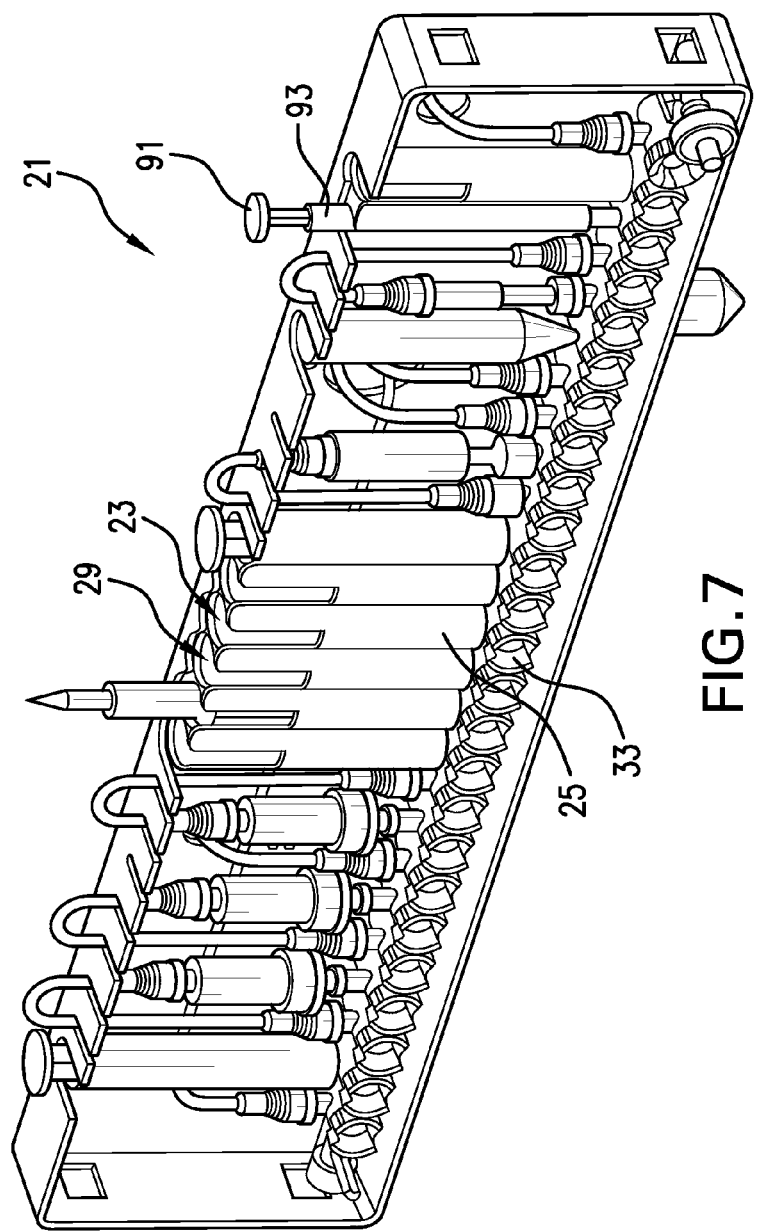
FIG. 7 shows a perspective view of a reagent cassette in accordance with an embodiment of the present invention.

FIG. 7 shows a perspective view of a reagent cassette 21 in accordance with an embodiment of the present invention. Reagent cassette 21 is intended to be used in an automated synthesis (not shown) unit provided with automated actuators. Reagent cassette 21 is cooperatively received in, engaged by, and operated by the automated synthesis unit. The automated synthesis unit cooperates with cassette 21 to produce various pharmaceutical or chemical products.

Cassette 21 has elongate body 210 which provides various components of fluid circuitry such as valves 212, conduit tubing 214, and actuator plungers 216. The valves 212 are desirable formed as taught in copending U.S. patent application Ser. No. 11/010142, entitled "Method and apparatus for the distribution of fluids", the entire contents of which are herein incorporated by reference as if fully disclosed herein. Body 210 defines a plurality of receptacles 220 for cooperatively receiving containers, eg, 222 which provide or accommodate contents used during a synthesis run. As the containers received in receptacles 220 include a puncturable cap 224, it is desirable that each receptacle 220 includes a blunt spike 226 (shown in phantom lines) for penetrating the puncturable cap 224 received therein. Each blunt spike 226 used provides the contents of the containers in fluid communication with the components of the fluid circuitry so as to be directable at the command of the automated synthesis unit. It has been found that incorporating the spike 226 of the present invention, cassette 21 increases operation reliability when producing product with the automated synthesis unit. Moreover, by providing spike 226 with a blunt end 228 which is symmetrical about the longitudinal axis X-X of the spike body 230, insertion of spike 226 through cap 224 does not tend to deflect off the axis X-X. Blunt end 228 desirably includes a solid planar end face 232 which extends transversely to axis X-X.

In a preferred embodiment of the present invention the diameter or width of the central bore of the spike is equal to half the maximum diameter or width of the spike. In a more preferable embodiment of the present invention the diameter or width of the central bore of the spike is less than half the maximum diameter or width of the spike. Preferably the maximum width or diameter of a spike is at least 2 mm and less than 10 mm. Additionally it is preferable that the length of a spike is less than 10 times its maximum width or diameter and more preferably less than 5 times its maximum width or diameter.

While the invention has been illustrated by examples relating to the use of a spike in a reagent cassette, spikes in accordance with the present invention can be used in other device where a spike has to penetrate a stopper.

The above mentioned embodiments are intended to illustrate the present invention and are not intended to limit the scope of protection claimed by the following claims.

What is claimed is:

1. A reagent cassette for an automated synthesis unit characterised in that it comprises an elongate body accommodating components of fluid circuitry, the body further defining at least one chamber for receiving a container having a puncturable cap, the chamber having a base supporting a spike for puncturing the puncturable cap of the container so as to render the interior of the container in fluid communication with at least a part of the fluid circuitry, wherein the chamber is sized to frictionally retain the container spaced from the spike and allows the container to be moved towards the base of the chamber so that the cap is punctured by the spike, wherein said spike (43, 53) comprises an elongated body (5) defining a longitudinal bore (31) and having a tip (47, 49) characterised in that said tip (47, 49) is blunt.

2. A method for penetrating the stopper of a container inserted into a reagent cassette for an automated synthesis unit comprising the steps of:
   providing a reagent cassette with a spike in accordance with claim 1;
   aligning the longitudinal axis of the stopper with the longitudinal axis of the spike; and
   moving said stopper towards said spike until the spike has penetrated the stopper.

3. The reagent cassette in accordance with claim 1 characterised in that said bore (31) is blocked at one end by a solid end surface (59) and said body (5) further defines at least one lateral opening (61) in fluid communication with bore (31).

4. The reagent cassette in accordance with claim 3, wherein the end surface (49) of each tip (47) is substantially flat and arranged to be substantially perpendicular to the longitudinal axis of the elongated body (5) of the spike.

5. The reagent cassette in accordance with claim 4, wherein the diameter of bore (31) is equal to or less than half the maximum diameter of said body (5).

6. The reagent cassette in accordance with claim 5, wherein said body (5) has a symmetrical transverse cross-section.

7. The reagent cassette in accordance with claim 6, wherein the body is formed of a semi-rigid polymer.

8. The reagent cassette of claim 5, wherein the diameter of the central bore of the spike is one half the maximum diameter of the spike.

9. The reagent cassette in accordance with claim 4, wherein the width of bore (31) is equal to or less than half the maximum width of said body (5).

10. The reagent cassette in accordance with claim 1, wherein said spike further comprises a reinforcing transverse rib that extends from one side of the bore of the spike to the opposite side.

11. The reagent cassette in accordance with claim 1, wherein said spike further comprises two mutually perpendicular reinforcing transverse ribs, each of said ribs extending from one side of the bore of said spike to the diametrically opposide side.

12. In a cassette adaptable to be received by a automated synthesis unit, wherein the cassette comprises an elongate body accommodating components of fluid circuitry, the body further defining at least one chamber for receiving a container having a puncturable cap, the chamber having a base supporting a spike, the spike having an elongate bore, for puncturing the puncturable cap of the container so as to render the interior of the container in fluid communication with at least a part of the fluid circuitry, wherein the chamber is sized to frictionally retain the container spaced from the spike and allows the container to be moved towards the base of the container so that the cap is punctured by the spike, the improvement comprising the at least one spike including a blunt tip which is symmetrical about the longitudinal axis of the spike for penetrating the puncturable cap.

13. The cassette of claim 12, wherein the spike further comprises an elongate hollow spike body, said spike body defining an aperture extending therethrough transversely to the longitudinal axis of the spike.

14. The cassette of claim 13, wherein the blunt tip of the spike further comprises a planar surface extending transversely to the longitudinal axis of the spike.

* * * * *